(12) United States Patent
Mathisen et al.

(10) Patent No.: US 10,722,336 B2
(45) Date of Patent: Jul. 28, 2020

(54) THREE-DIMENSIONAL MEDICAL IMPLANT

(71) Applicant: NOVUS SCIENTIFIC AB, Uppsala (SE)

(72) Inventors: Torbjörn Mathisen, Älvsjö (SE); Anna Wistrand, Vällingby (SE)

(73) Assignee: NOVUS SCIENTIFIC AB, Uppsala (SE)

( * ) Notice: Subject to any disclaimer, the term of this patent is extended or adjusted under 35 U.S.C. 154(b) by 149 days.

(21) Appl. No.: 15/938,125

(22) Filed: Mar. 28, 2018

(65) Prior Publication Data

US 2018/0228598 A1  Aug. 16, 2018

Related U.S. Application Data

(63) Continuation-in-part of application No. 15/569,479, filed as application No. PCT/EP2016/072448 on Sep. 21, 2016, now abandoned.

(Continued)

(51) Int. Cl.
*A61F 2/12* (2006.01)
*A61F 2/08* (2006.01)
(Continued)

(52) U.S. Cl.
CPC ............ *A61F 2/0063* (2013.01); *A61B 90/02* (2016.02); *A61F 2/0059* (2013.01); *A61F 2/08* (2013.01); *A61F 2/12* (2013.01); *A61L 27/18* (2013.01); *A61L 27/20* (2013.01); *A61L 27/222* (2013.01); *A61L 27/225* (2013.01); *A61L 27/24* (2013.01); *A61L 27/48* (2013.01); *A61L 27/52* (2013.01); *A61L 27/56* (2013.01); *A61L 27/58* (2013.01);
(Continued)

(58) Field of Classification Search
CPC . A61F 2/12; A61F 2/0063; A61F 2002/30062
USPC ....................................................... 623/7–8
See application file for complete search history.

(56) References Cited

U.S. PATENT DOCUMENTS 3,902,497 A   9/1975  Casey
4,186,448 A   2/1980  Brekke
(Continued)

FOREIGN PATENT DOCUMENTS

EP     2 762 172 A1    8/2014
WO   WO-2010/006270 A1   1/2010
WO   WO-2011/003422 A1   1/2011

OTHER PUBLICATIONS

Joseph J. Kim et al., Vascularization of Three-Dimensional Engineered Tissues for Regenerative Medicine Applications, Acta Biomaterialia, vol. 41, Jun. 2, 2016, pp. 17-26.

(Continued)

*Primary Examiner* — Suzette J Gherbi
(74) *Attorney, Agent, or Firm* — Foley & Lardner LLP

(57) ABSTRACT

The present disclosure relates to a three-dimensional, degradable medical implant for regeneration of soft tissue comprising a plurality of volume-building components and a mesh component which is substantially made of monofilament or multifilament fibers, wherein each volume-building component is attached to at least one point on a surface of the mesh component, and wherein the projected surface area of each volume-building component, when projected on the surface of the mesh component, corresponds to a maximum of one tenth of the surface area of the mesh component.

24 Claims, 6 Drawing Sheets

Related U.S. Application Data

(60) Provisional application No. 62/222,571, filed on Sep. 23, 2015.

(51) Int. Cl.
| | | |
|---|---|---|
| *A61L 27/56* | (2006.01) | |
| *A61F 2/00* | (2006.01) | |
| *A61L 27/52* | (2006.01) | |
| *A61L 27/58* | (2006.01) | |
| *A61L 27/48* | (2006.01) | |
| *A61B 90/00* | (2016.01) | |
| *A61L 27/18* | (2006.01) | |
| *A61L 27/20* | (2006.01) | |
| *A61L 27/22* | (2006.01) | |
| *A61L 27/24* | (2006.01) | |
| *B32B 5/02* | (2006.01) | |
| *B32B 5/26* | (2006.01) | |
| *D04B 21/12* | (2006.01) | |
| *D04B 21/20* | (2006.01) | |
| *B33Y 80/00* | (2015.01) | |

(52) U.S. Cl.
CPC .............. *B32B 5/026* (2013.01); *B32B 5/028* (2013.01); *B32B 5/26* (2013.01); *D04B 21/12* (2013.01); *D04B 21/20* (2013.01); *A61F 2002/0068* (2013.01); *A61F 2002/0086* (2013.01); *A61F 2002/0894* (2013.01); *A61F 2210/0004* (2013.01); *A61F 2210/0076* (2013.01); *A61F 2230/0021* (2013.01); *A61F 2230/0069* (2013.01); *A61F 2230/0082* (2013.01); *A61F 2230/0091* (2013.01); *A61F 2230/0093* (2013.01); *A61F 2240/001* (2013.01); *A61F 2250/0018* (2013.01); *A61L 2430/04* (2013.01); *A61L 2430/10* (2013.01); *A61L 2430/24* (2013.01); *A61L 2430/34* (2013.01); *B32B 2250/20* (2013.01); *B32B 2307/7163* (2013.01); *B32B 2535/00* (2013.01); *B33Y 80/00* (2014.12); *D10B 2401/10* (2013.01); *D10B 2401/12* (2013.01); *D10B 2509/00* (2013.01)

(56) References Cited

U.S. PATENT DOCUMENTS

| | | |
|---|---|---|
| 5,514,181 A | 5/1996 | Light et al. |
| 2012/0010636 A1 | 1/2012 | Boey et al. |
| 2012/0143329 A1 | 6/2012 | Kim |
| 2014/0222161 A1* | 8/2014 | Mathisen ............... A61F 2/0077 623/23.72 |
| 2014/0303465 A1* | 10/2014 | Simpson ............ A61B 5/14532 600/347 |
| 2015/0297798 A1* | 10/2015 | Badylak .................. A61L 31/06 600/37 |
| 2016/0022866 A1* | 1/2016 | Liu .......................... A61L 27/50 427/2.24 |
| 2016/0095695 A1* | 4/2016 | Altman ............... A61K 38/1767 623/8 |
| 2017/0128015 A1* | 5/2017 | Rogers ................. A61B 5/6868 |
| 2017/0218228 A1* | 8/2017 | Jose ........................ C09D 11/03 |
| 2017/0273775 A1* | 9/2017 | Rocco .................... A61F 2/0077 |
| 2018/0008176 A1* | 1/2018 | Simpson ............ A61B 5/14532 |
| 2018/0050130 A1* | 2/2018 | Jiang ...................... A61L 27/16 |
| 2018/0064931 A1* | 3/2018 | Clements ............. A61B 5/6882 |
| 2018/0228598 A1* | 8/2018 | Mathisen ................ A61L 27/58 |
| 2018/0325644 A1* | 11/2018 | Felix ....................... B29C 48/25 |
| 2019/0269822 A1* | 9/2019 | Williams ................ A61L 27/56 |

OTHER PUBLICATIONS

Nick A. Sears et al., A Review of Three-Dimensional Printing in Tissue Engineering, Tissue Engineering: Part B, vol. 22, No. 4, Apr. 8, 2016, pp. 298-311.

Xingang Wang et al., Applications of Knitted Mesh Fabrication Techniques to Scaffolds for Tissue Engineering and Regenerative Medicine, Journal of the Mechanical Behavior of Biomedical Materials, vol. 4, Apr. 19, 2011, pp. 922-932.

USPTO Office Action, U.S. Appl. No. 15/569,479, dated Mar. 5, 2019, 8 pages.

* cited by examiner

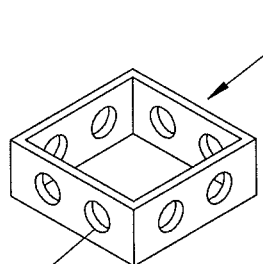
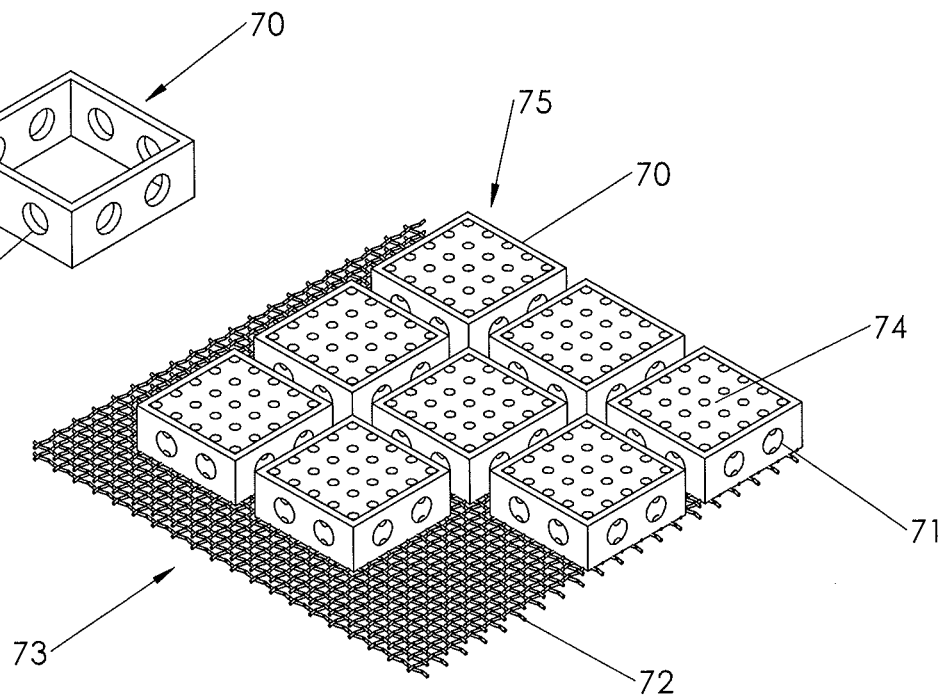
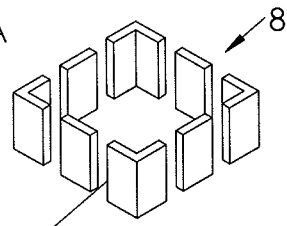
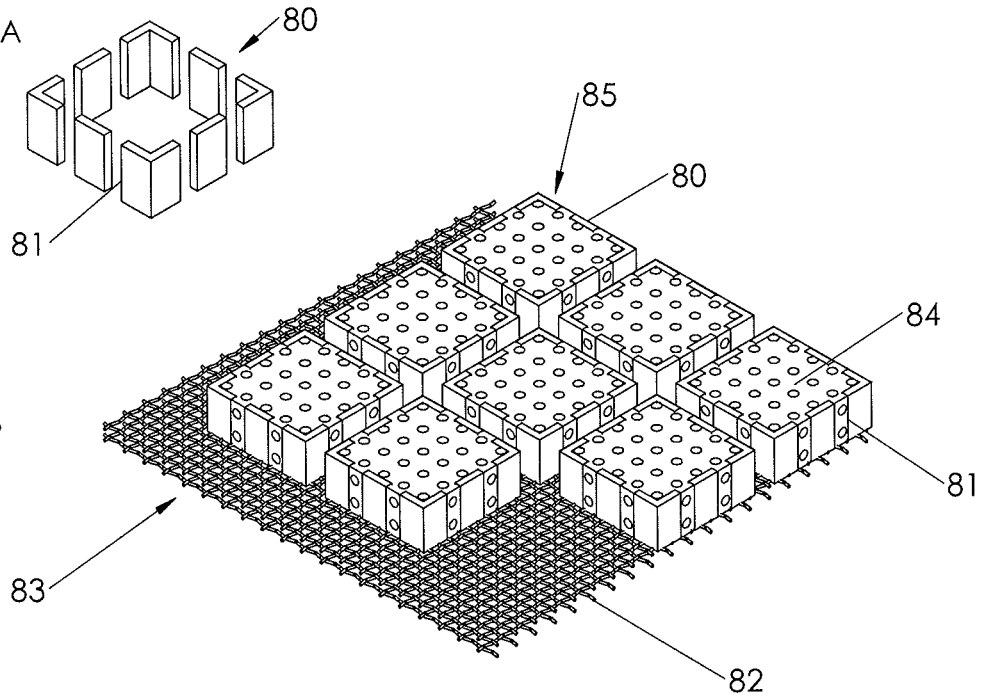

THREE-DIMENSIONAL MEDICAL IMPLANT

CROSS REFERENCE TO RELATED APPLICATIONS

This application is a continuation-in-part of U.S. application Ser. No. 15/569,479, filed on Oct. 26, 2017, which is the National Stage Application of PCT/EP2016/072448, filed on Sep. 21, 2016, which claims benefit of priority from Provisional Application No. 62/222,571, filed on Sep. 23, 2015; the entire contents of all of which are incorporated herein by reference.

FIELD OF THE INVENTION

The present disclosure relates to the field of medical technology, in particular to a three-dimensional degradable medical implant for regeneration of soft tissue. The medical implant comprises a plurality of volume-building components and a mesh component which is substantially made of monofilament or multifilament fibers. The projected surface area of each volume-building component, when projected on the surface of the mesh component, is substantially smaller than the surface area of the mesh component.

BACKGROUND OF THE INVENTION

Degradable polymers like polyesters and polycarbonates have been used for years within the medical device industry as sutures and various fixation devices such as plates, pins and screws to hold small bone fragments together during healing. The activity in the field of three-dimensional (3D) scaffolding structures for the purpose of bridging tissue gaps and giving the cells a scaffold to populate and proliferate on has been considerable, especially in the last 15 years. However, the limited number of such devices in today's market indicates the difficulty in providing a scaffold that fits the surgeons' needs in terms of tissue regeneration, ease of use and problem-free healing. One of the very first patent applications describing a porous 3D structure using synthetic degradable polymers was filed in 1974, U.S. Pat. No. 3,902,497, disclosing an absorbable sponge that could be used as a hemostatic and left to degrade and disappear inside the human body. In 1977 another application was filed, U.S. Pat. No. 4,186,448, describing a porous plug for regeneration of bone in bone defects or voids. This can be said to be the beginning of the search of synthetic degradable scaffolds that would support cells during the early phase of proliferation, and which also provided voids in form of interconnected pores to allow for a homogeneous population of the entire scaffold. Today, still the same technique is used and explored by thousands of researchers all over the world in search for the ultimate scaffold. The methods of making porous scaffolds have been greatly refined over the last years and several techniques are available. New emerging techniques such as 3D printing, 3D knitting and electrospinning to mention a few are actively being explored in new scaffolds for various tissue engineering applications with various results (Sears N. A. et al., Tissue Engineering: Part B, Volume 22, Number 4, pages 298-311, 2016; Kim J. J. et al., Acta Biomaterialia, Volume 41, pages 17-26, 2016; Wang X. et al., Journal of the mechanical behavior of biomedical materials, Volume 4, pages 922-932, 2011). In US20140222161A1, U.S. Pat. No. 5,514,181, and US20120010636A1, other types of three-dimensional medical implants are described.

One of the greatest challenges for the perfect scaffold is that it shall combine an adequate modulus required by the surrounding tissue to avoid modulus mismatch and at the same time have an open structure to allow for tissue ingrowth and vascularization to avoid apoptosis in the scaffold interior.

Furthermore, it is difficult to combine different scaffold characteristics or even different materials into one scaffold since porous materials made by solid leaching or phase separation techniques do yield a very similar structure throughout the entire scaffold. With the use of 3D printing we may overcome the difficulty in combining different materials and also different designs into one scaffold. There are however still several obstacles to overcome before it is possible to make scaffolds which possess a certain predefined design, which are easy to apply/adapt at the defect site and which have the required mechanical strength needed for various specific clinical defects.

The lack of pliability is often a tradeoff since the scaffold needs to possess certain rigidity in order for the matrix to withstand the natural load situation over the scaffold after implantation. Especially in soft tissue applications, the scaffold should be resilient enough to follow the load situation and to regain shape with minimal hysteresis when no load is acting upon it until the scaffold has been fully populated by cells overtaking the load supporting function. For hard tissue applications, pliability is not such a concern but the concept of using different materials and designs to achieve different clinical results at various sections of the scaffold is still an unsolved challenge, i.a. soft tissue integration and anchoring of the device in one section and bone tissue regeneration in the other section. Current research within material and/or processing technology have not yet been able to mimic the properties of a fully functional matrix for soft tissue regeneration which, from a doctor's perspective should be easy to apply, should have minimal modulus mismatch and possess pliable and resilient properties without compromising with the mechanical requirements.

Modern hydrogels may seem to be the perfect choice of soft and resilient biomaterial, but they are fragile with poor mechanics and must be made and used at the bedside. Some of them can be freeze dried and rehydrated before use, but this presents the doctor with additional work and distraction from the patient and the ongoing surgery. The lack of possibility to anchor/fasten the hydrogel matrix is another great drawback with these types of scaffolds since most scaffolds will need suturing or some kind of tacks to keep them in place until it is anchored by new tissue deposited within the scaffold.

Current degradable scaffolds or matrices, aimed at short term support during repair or regeneration of new tissue in various clinical defects, have several drawbacks and among them is the lack of pliability of most scaffolds. Lack of pliability often leads to an overall modulus mismatch with surrounding tissue that may trigger an excess of inflammatory reactions that may compromise the early healing process. A prerequisite for a functional scaffold is to provide space for new tissue to populate. If the scaffold is made too soft or pliable there is an ultimate risk for collapse of the porous structure especially if the clinical situation exposes the scaffold to static or dynamic loads. With current processes for making porous scaffolds which can be used for tissue regeneration or augmentation there are also limitations when it comes to fabrication of multilayer, gradient or multiphase scaffolds that could exhibit different physiochemical properties in various sections of the scaffold.

SUMMARY OF THE INVENTION

Consequently, there is still a need for further three-dimensional medical implants having a structure which allows rapid tissue ingrowth in combination with possessing adequate pliability and mechanical rigidity for different implant applications within the human or animal body.

The above objects are achieved by a three-dimensional, degradable medical implant as described herein. To overcome some of the shortcomings mentioned above it is suggested to combine the pliability found in knitted meshwork based upon fibers, such as multifilaments or soft monofilaments, with the mechanical rigidity of a plurality of volume-building components that are attached to the mesh structure. The volume-building components are optionally load-bearing.

The present disclosure relates to a three-dimensional, degradable medical implant for regeneration of soft tissue comprising a plurality of volume-building components and a mesh component which is substantially made of monofilament or multifilament fibers, wherein each volume-building component is attached to at least one point on a surface of the mesh component, and wherein the projected surface area of each volume-building component, when projected on the surface of the mesh component, corresponds to a maximum of one tenth of the surface area of the mesh component.

The medical implant according to the present disclosure may further comprise a second mesh component, which is attached to at least two of the first plurality of volume-building components, to create a sandwich structure. Additionally, it may comprise a second plurality of volume-building components, wherein each of the second plurality of volume-building components is attached to at least one surface of the second mesh component, to create a sandwich structure.

The present disclosure also relates to a use of a medical implant to stabilize a breast prosthesis and to provide space between flap tissue and the breast prosthesis to allow for tissue regeneration, wherein the medical implant is placed in close apposition to the breast prosthesis.

The present disclosure further relates to a method for breast reconstruction in an individual, comprising placing a medical implant according to any one of claims 1-24 in close apposition to a breast prosthesis in the individual to stabilize the breast prosthesis and to provide space between flap tissue and the breast prosthesis to allow for tissue regeneration.

In the present text, the term "soft tissue" is defined as including the tissues that connect, support, or surround other structures and organs of the body, not being hard tissue such as bone. Soft tissue includes tendons, ligaments, fascia, skin, fibrous tissues, fat, and synovial membranes (which are connective tissue), and muscles, nerves and blood vessels (which are not connective tissue). Soft tissue may also be defined as nonepithelial, extraskeletal mesenchyme exclusive of the reticuloendothelial system and glia.

BRIEF DESCRIPTION OF THE DRAWINGS

FIG. 7A: Perspective view of a support structure.
FIG. 7B: Perspective view of a three-dimensional medical implant.

FIG. 8A: Perspective view of a support structure.
FIG. 8B: Perspective view of a three-dimensional medical implant.

DETAILED DESCRIPTION OF THE INVENTION

Figure 1A:
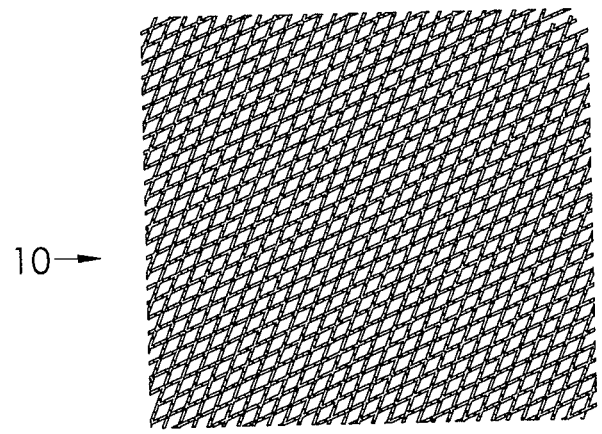
FIG. 1A: Schematic drawing of a mesh which has rhombic or diamond-shaped openings. The mesh as such is previously known in the art.

FIG. 1A illustrates schematically a mesh 10 which has rhombic or diamond-shaped openings, which may be obtained by warp knitting using atlas type pattern or interlaced pillar pattern. The mesh as such is previously known in the art.

Figure 1B:
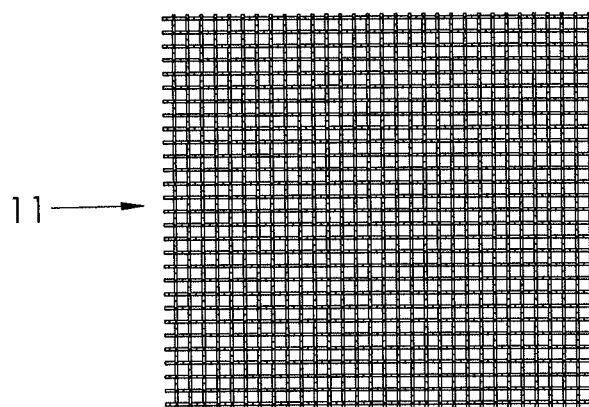
FIG. 1B: Schematic drawing of a mesh which has square-shaped openings. The mesh as such is previously known in the art.

FIG. 1B illustrates schematically a mesh 11 which has square-shaped openings, which may be obtained by open woven structure or warp knitting using double marquisette combined with pillar stitch. The mesh as such is previously known in the art.

Figure 1C:
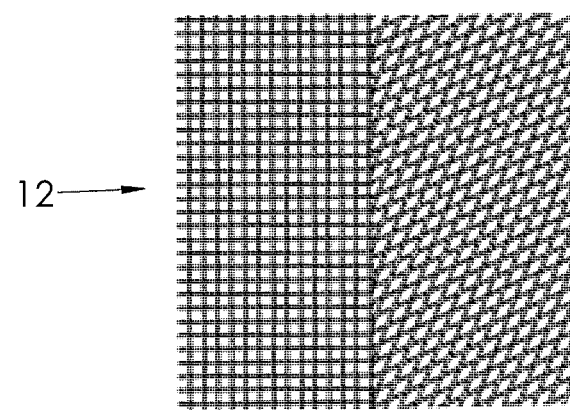
FIG. 1C: Schematic drawing of a mesh which is a combination of a previously known mesh with rhombic or diamond-shaped openings and a previously known mesh with square-shaped openings.

FIG. 1C illustrates schematically a mesh 12 which is a combination of a mesh 10 and a mesh 11.

Figure 2A:
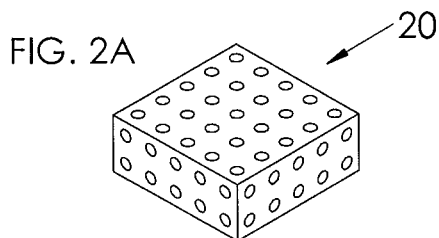
FIG. 2A: Perspective view of a volume-building component.

FIG. 2A illustrates schematically a perspective view of a volume-building component 20 according to the present disclosure consisting of a scaffold component. The dotted pattern of the volume-building component is not to be construed as illustrating holes or pores in the material, but is solely meant to illustrate any type of volume-building component, irrespective of the structure or composition of the volume-building component. The same definition applies to the dotted pattern of the volume-building components in FIGS. 2B, 3, 4, 5, 6, 7B, and 8B.

Figure 2B:
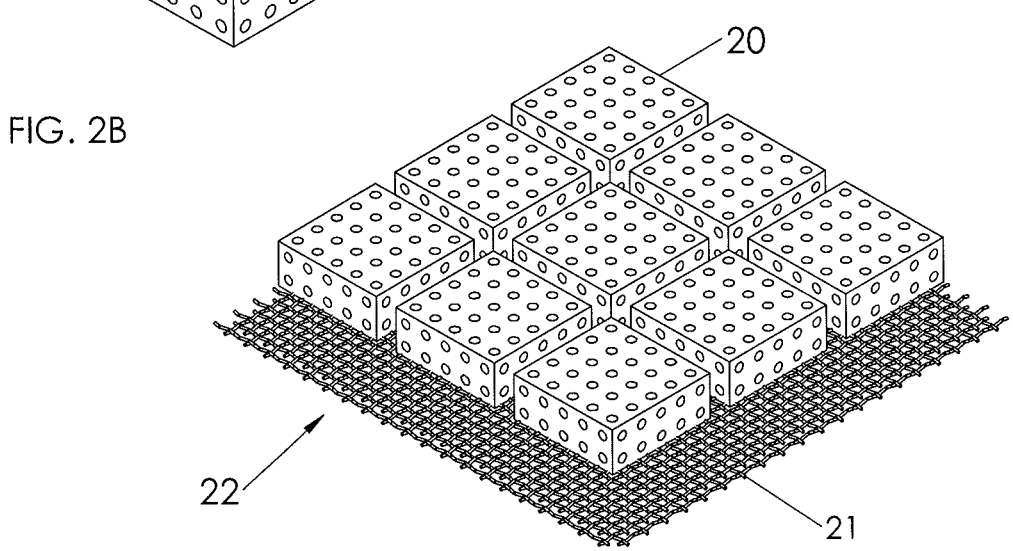
FIG. 2B: Perspective view of a three-dimensional medical implant.

FIG. 2B illustrates schematically a perspective view of a three-dimensional medical implant 22 according to the present disclosure, comprising a mesh component 21 and a plurality of volume-building components 20 consisting of scaffold components.

Figure 3:
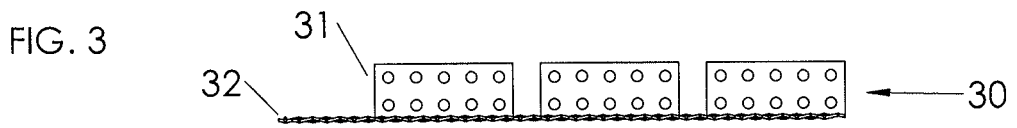
FIG. 3: Side view of a three-dimensional medical implant.

FIG. 3 illustrates schematically a side view of a three-dimensional medical implant 30 according to the present disclosure, comprising a first mesh component 32 and a first plurality of volume-building components 31 consisting of scaffold components which are attached to a first surface of the mesh component 32.

Figure 4:
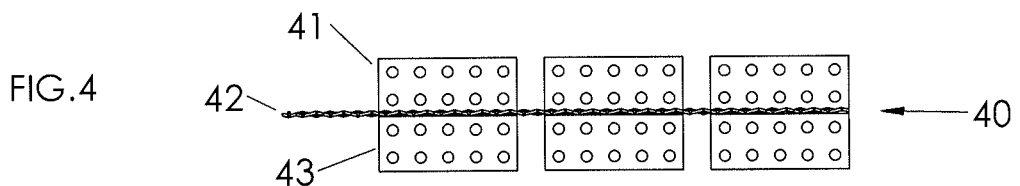
FIG. 4: Side view of a three-dimensional medical implant.

FIG. 4 illustrates schematically a side view of a three-dimensional medical implant 40 according to the present disclosure, comprising a first mesh component 42, a first plurality of volume-building components 41 which are attached to a first surface of the first mesh component 42, and a second plurality of volume-building components 43 which are attached to a second surface of the first mesh component 42.

Figure 5:
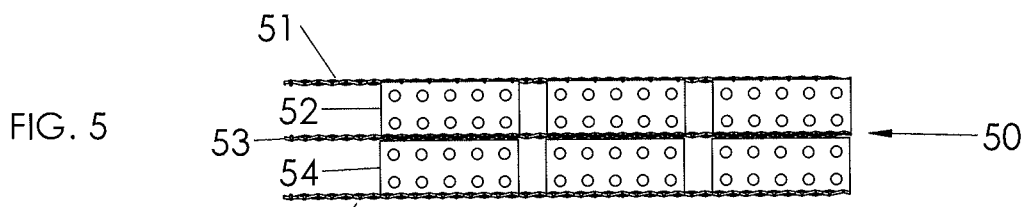
FIG. 5: Side view of a three-dimensional medical implant.

FIG. 5 illustrates schematically a side view of a three-dimensional medical implant 50 according to the present disclosure, comprising a first mesh component 51, a first plurality of volume-building components 52 which are attached to a first surface of the first mesh component 51, a second mesh component 53 which is attached to the first plurality of volume-building components 52, a second plurality of volume-building components 54 which are attached to a first surface of the second mesh component 53, and a third mesh component 55 which is attached to the second plurality of volume-building components 54.

Figure 6:
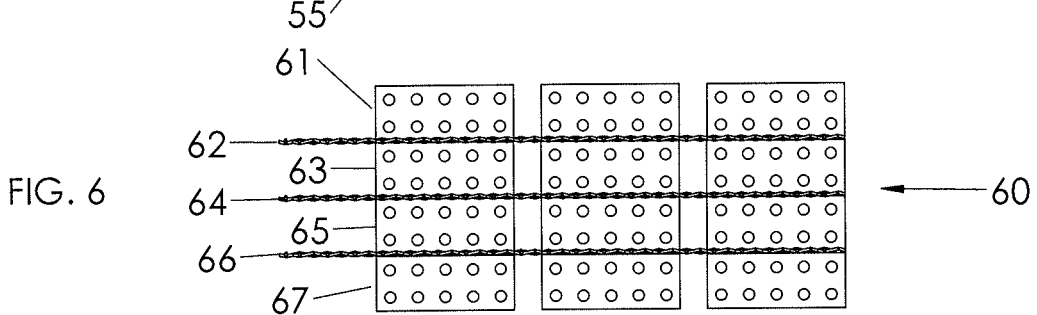
FIG. 6: Side view of a three-dimensional medical implant.

FIG. 6 illustrates schematically a side view of a three-dimensional medical implant 60 according to the present disclosure, comprising a first mesh component 62, a first plurality of volume-building components 61 which are attached to a first surface of the first mesh component 62, a second plurality of volume-building components 63 which are attached to a second surface of the first mesh component 62, a second mesh component 64 which is attached to the second plurality of volume-building components 63, a third plurality of volume-building components 65 which are attached to a first surface of the second mesh component 64, a third mesh component 66 which is attached to the third plurality of volume-building components 65, and a fourth plurality of volume-building components 67 which are attached to a second surface of the third mesh component 66.

FIG. 7A illustrates schematically a perspective view of a hollow, frame-shaped support structure 70 to be included in a volume-building component according to the present disclosure, which support structure has pores, holes, or through-holes 71 in its walls.

FIG. 7B illustrates schematically a perspective view of a three-dimensional medical implant 73 according to the present disclosure, comprising a mesh component 72 and a plurality of volume-building components 75, each volume-building component 75 comprising a scaffold component 74 and a frame-shaped support structure 70 having pores, holes or through-holes 71 in its walls surrounding the scaffold component 74.

FIG. 8A illustrates schematically a perspective view of a hollow, frame-shaped support structure 80 to be included in a volume-building component according to the present disclosure, which support structure 80 has slits 81 in its walls.

FIG. 8B illustrates schematically a perspective view of a three-dimensional medical implant 83 according to the present disclosure, comprising a mesh component 82 and a plurality of volume-building components 85, each volume-building component 85 comprising a scaffold component 84 and a frame-shaped support structure 80 having slits 81 in its walls surrounding the scaffold component 84.

Figure 9A:
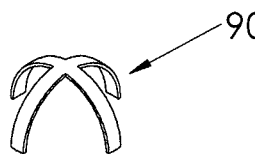
FIG. 9A: Perspective view of a support structure.

FIG. 9A illustrates schematically a perspective view of a hollow, dome-shaped support structure 90 to be included in a volume-building component according to the present disclosure.

Figure 9B:
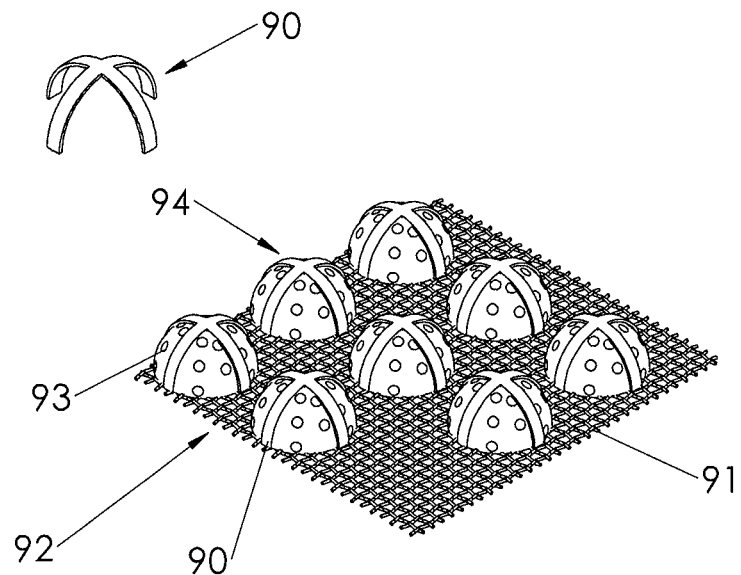
FIG. 9B: Perspective view of a three-dimensional medical implant.

FIG. 9B illustrates schematically a perspective view of a three-dimensional medical implant 92 according to the present disclosure, comprising a mesh component 91 and a plurality of volume-building components 94, each volume-building component 94 comprising a scaffold component 93 and a dome-shaped support structure 90 surrounding the scaffold component 93.

Figure 10A:
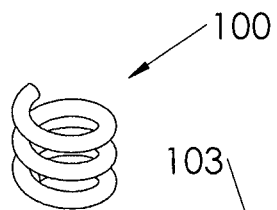
FIG. 10A: Perspective view of a support structure.

FIG. 10A illustrates schematically a perspective view of a hollow, spring-shaped support structure 100 to be included in a volume-building component according to the present disclosure. This is an example of a resilient support structure, which may have many different shapes but will act as a cushion and allow certain deformation of the 3D medical implant.

Figure 10B:
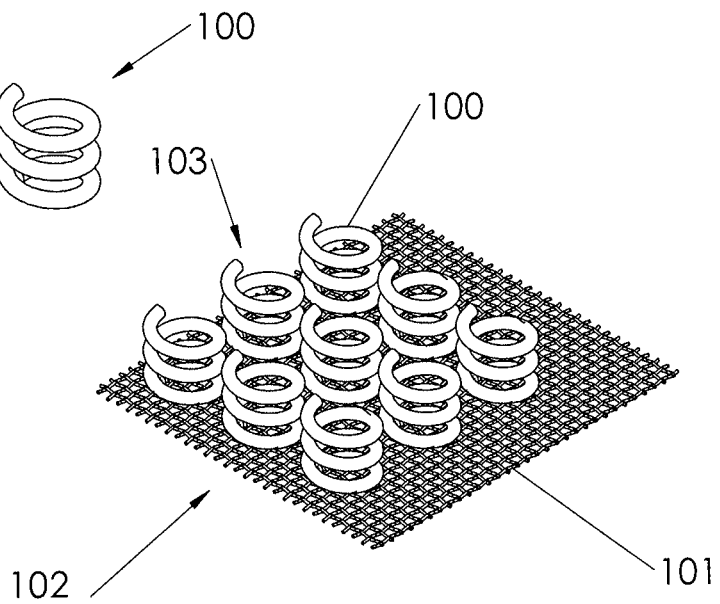
FIG. 10B: Perspective view of a three-dimensional medical implant.

FIG. 10B illustrates schematically a perspective view of a three-dimensional medical implant 102 according to the present disclosure, comprising a mesh component 101 and a plurality of volume-building components 103, each volume-building component 103 comprising a spring-shaped support structure 100. In accordance with the present disclosure, each volume-building component 103 also comprises a scaffold component inside the spring-shaped support structure 100. The scaffold components have been omitted in FIG. 10B for increased visibility of the overall medical implant 102.

Figure 11:
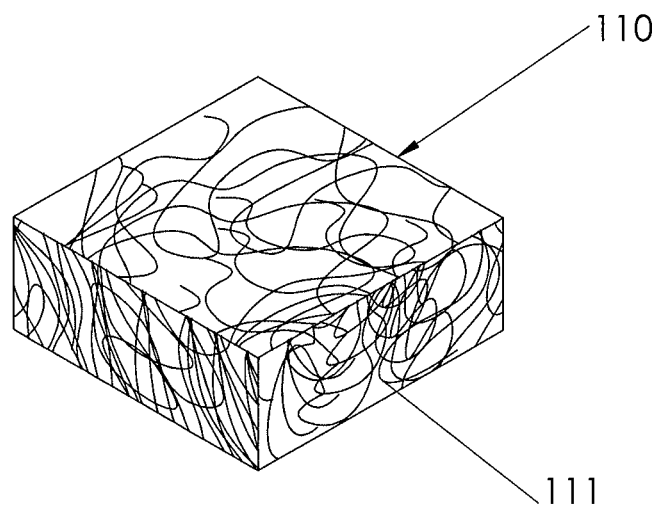
FIG. 11: Perspective view of a scaffold component.

FIG. 11 illustrates schematically a perspective view of a scaffold component 110 to be included in a volume-building component according to the present disclosure. The material 111 of the scaffold component 110 is substantially homogeneous, and may be exemplified by a degradable hydrogel as described in more detail elsewhere in this text.

Figure 12:
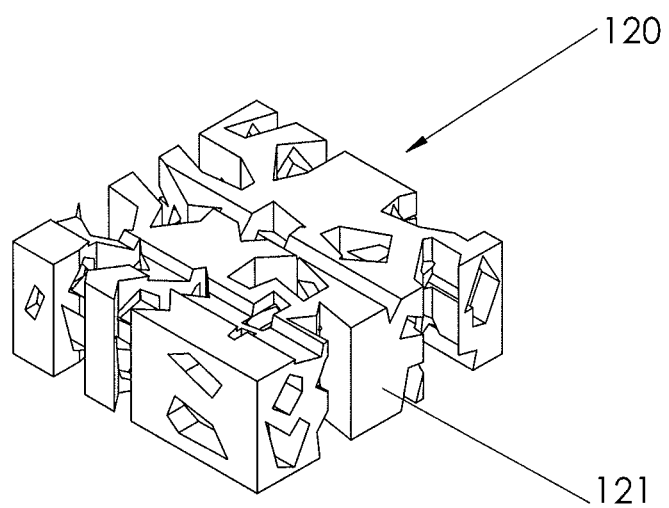
FIG. 12: Perspective view of a scaffold component.

FIG. 12 illustrates schematically a perspective view of a scaffold component 120 to be included in a volume-building component according to the present disclosure. The material 121 of the scaffold component 120 is substantially porous, and may be exemplified by a degradable polymer, which may be made porous by a plurality of methods. Suitable materials and manufacturing methods are described in more detail elsewhere in this text.

Figure 13:
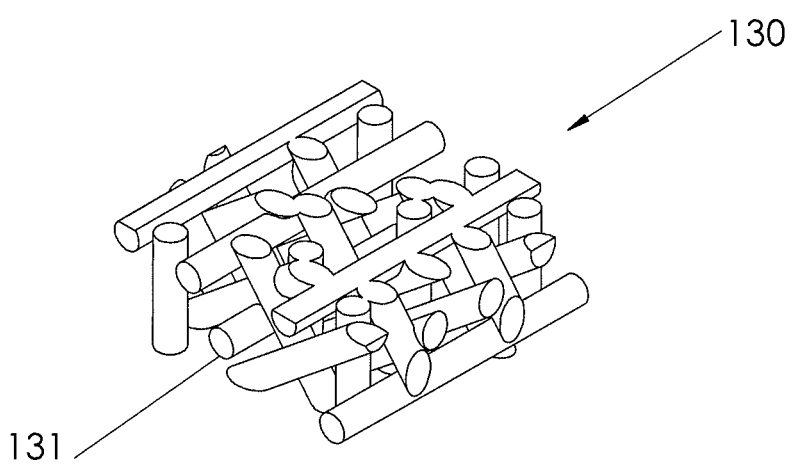
FIG. 13: Perspective view of a scaffold component.

FIG. 13 illustrates schematically a perspective view of a scaffold component 130 to be included in a volume-building component according to the present disclosure. The material 131 of the scaffold component 130 is substantially fibrous, and may be exemplified by degradable fibers as described in more detail elsewhere in this text.

Figure 14A:
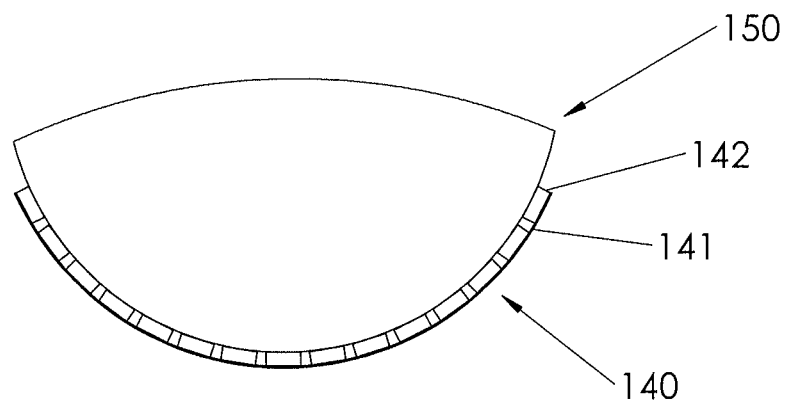
FIG. 14A: Front view of a three-dimensional medical implant.

FIG. 14A illustrates schematically a front view of a three-dimensional medical implant 140 according to the present disclosure, comprising a mesh component 141 and a plurality of volume-building components 142 which are attached to a first surface of the mesh component 141. The medical implant 140 is applied around the lower side of a breast prosthesis 150.

Figure 14B:
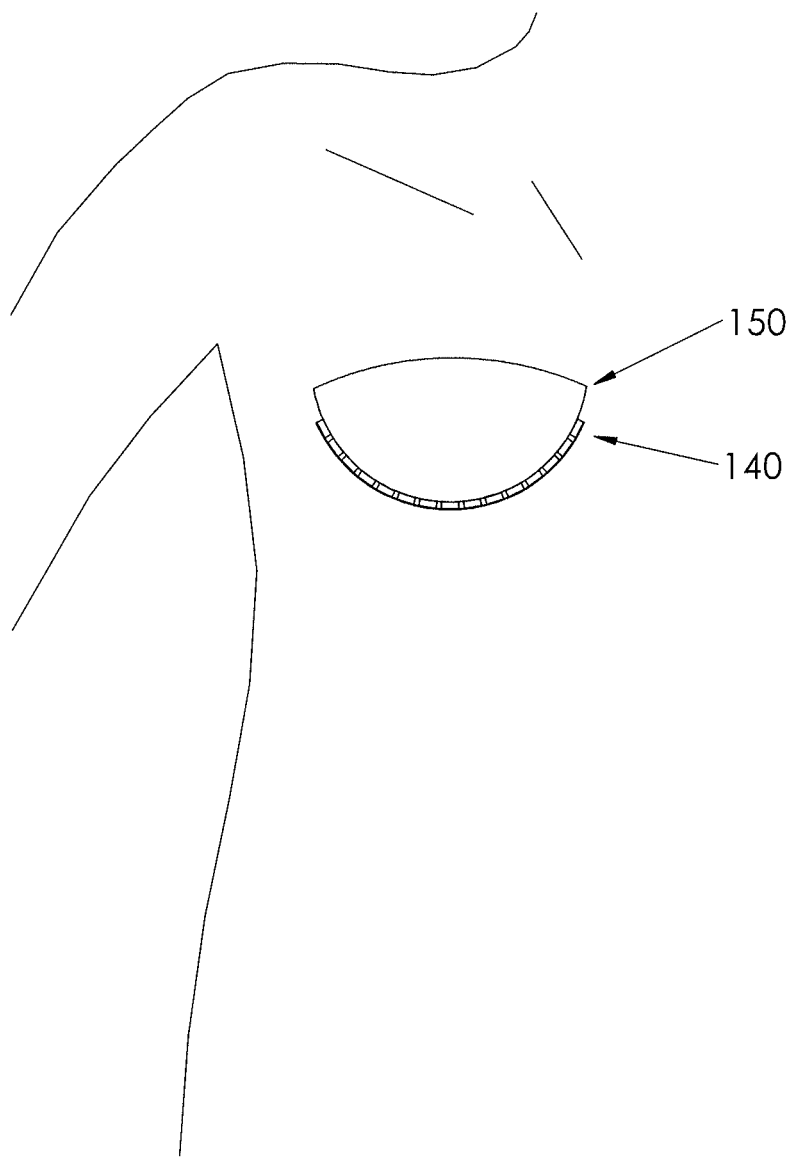
FIG. 14B: Front view of a three-dimensional medical implant.

FIG. 14B illustrates schematically a front view of the three-dimensional medical implant 140 applied below a breast prosthesis 150 according to FIG. 14A, as seen in an implanted state in a body.

In all of the above illustrations of the present disclosure, an important feature is that the volume building components are spaced apart so as to provide a pliable medical implant with an open structure for easy ingrowth of cells and vessels. The volume building components are also a key component for providing and securing space into which new tissue can grow. The mesh can be made from monofilament or multifilament fibers through a number of manufacturing methods, can be degradable, can be knitted, woven, non-woven, meltblown, electrospun and/or similar. Furthermore, flexible materials may be molded into a similar framework with or without fibers as armoring inside to provide a flexible base onto which volume building components can be 3D printed. The volume building components can have several shapes and properties depending on the clinical need. FIGS. 7A, 8A, 9A, and 10A show examples of different hollow-shaped support structures ("cages") that can be used over an entire surface of the mesh or only on certain parts of a surface of the mesh. The support structures are filled with scaffold components which promote cell growth. Such scaffold components may be, but are not limited to, fine fibrous nonwoven structures or random electrospun fibers but can also be collagen or any other synthetic or natural hydrogel. The scaffold component will be protected from deformation due to external load of surrounding tissue by the support structure, which acts as a protective means around the fragile fiber or hydrogel structure. The medical implant can, as illustrated in FIGS. 3, 4, 5, 6 be furnished with several mesh components and several pluralities of volume-building components. The medical implant can have equally or differently designed volume-building components in different sections of the medical implant to provide support and/or guidance for different tissues within the same defect area in the body. The medical implant can also be folded or rolled into a tube or rod-shaped construct (not shown in any figure).

In the following, the medical implant according to the present disclosure will be described in more detail.

Design of the Three-Dimensional Medical Implant

The three-dimensional, degradable medical implant (herein also referred to as a three-dimensional or 3D matrix) according to the present disclosure comprises one or more degradable mesh components joined together by small, degradable volume-building components which are spread in a regular or random fashion over the entire mesh surface or only part of the surface. The shortest distance between two volume-building components should be no smaller than 0.2 mm but is more preferably found in the interval including from 0.3 to 3.0 mm and is no larger than 5.0 mm. Each volume-building component can be connected to the mesh by its entire surface or only part of the surface to the underlying or overlying mesh but can also have only one contact point in order to increase mobility and thus increase the adaptability of the 3D matrix to the surrounding tissues or implant. The smallest point of contact visualized can be that of a mono- or multifilament running through the volume-building component and knitted or sewed into the mesh on one or both sides of the volume-building component. The use of only one loose contact point will further decrease the radius of curvature obtainable and thus increase the mobility of the scaffold component.

The 3D matrix can optionally have volume-building components on both sides of the mesh. Such volume-building components can be mirror images of each other or displaced in any direction on the mesh surface. The volume-building components can be arranged in an orderly or repeatable pattern but can also be placed randomly across the surface of the first mesh component and in a different arrangement on the surface of the second mesh component being linked to the volume-building components found on the surface of the first mesh surface. Another possibility is to have different volume-building components on different side of a mesh, which gives the mesh different properties on each side.

Each volume-building component comprises a degradable scaffold component, and optionally further comprises a degradable, hollow support structure which surrounds the scaffold component at least partly. The support structure may be hollow, frame-shaped and open at the top, and thus enclose the scaffold component by its side walls but the top surface of the scaffold component is directly exposed to the surrounding tissue when implanted. Alternatively, the support structure may be hollow and dome-shaped, in which case it encloses the scaffold component by its two arches forming a cross at the top, but leaving most of the scaffold component directly exposed to the surrounding tissue when implanted. In a further embodiment, the support structure may be hollow, spring-shaped and open at the top, which means that it will enclose the scaffold component by its spiral-shaped structure but otherwise leave the scaffold component directly exposed to the surrounding tissue when implanted. As mentioned above, this is an example of a resilient support structure, which will act as a cushion and allow certain deformation of the 3D medical implant. Such deformation (movements) of the 3D medical implant is important for cells to deposit the right type of extracellular matrix, through a mechanism known as mechano-transduction.

In those cases where the 3D matrix is made with two or more mesh components, the distance between any two mesh components should be at least 2.0 mm and maximum 10.0 mm, more preferably in the range including from 2.0 to 5.0 mm. The 3D matrix may be built up by as many as 5 mesh components, each having volume-building components attached to at least one surface. Each volume-building component comprises a scaffold component with or without support structure. The different mesh components are linked together through the scaffold components or their support structure.

The maximum thickness of the 3D matrix is 30.0 mm, and preferably does not exceed 15.0 mm. The 3D matrix has a maximum surface area of 600 cm$^2$.

Design of Volume-Building Components

Support Structure

As described above, the three-dimensional degradable medical implant (or matrix) according to the present disclosure comprises a plurality of degradable volume-building components, each of which comprises a degradable scaffold component and optionally further comprises a degradable support structure. The volume-building components can have different outer shapes and different interior composition, due to the shape and composition of the scaffold components and support structures, depending on different clinical applications. The support structure is characterized by having a higher compression modulus than the scaffold components. Herein, by compression modulus is meant the capacity of a material to withstand loads acting upon the surface (and tending to reduce the size) of the material, independent of any pores or openings present in the surface segment of the material upon which the load is acting. The support structure is typically produced from degradable polymers made from lactide, glycolide, paradioxanone, ε-caprolactone, trimethylene carbonate or any combination thereof in random or block copolymers.

Such polymers are typically rigid due to their semi-crystalline nature, but also amorphous variants such as poly-D,L-lactide and certain amorphous copolymers between D,D- and L,L-lactide can be used due to their high glass transition temperature (Tg), which needs to be above 40° C. The support structure is most conveniently 3D printed using any type of 3D printers such as those feed with monofilament, pellets or solutions of the polymer to be printed but can also be extruded as a hollow structure, having a variety of different cross sections such as round, square and triangular shaped to mention an few, with subsequent after-treatment such as sawing or drilling to achieve slits or holes for the tissue to communicate with the volume-building component. A particularly useful technique to achieve slits, holes or partly surface etching in degradable polymers such as those used in the support structure is the use of lasers. Especially various kinds of lasers such as but not limited to excimer lasers using short wavelengths such as 248 nm or lower is useful since they allow for removal of material from resorbable polymers of the kind mentioned above without unnecessary temperature increases in the material. Further techniques that can be used to produce support structures are injection molding or compression molding. To allow for an extra deformation of the 3D medical implant in certain places or over the whole surface, the support structure can take the form of a dome or an arch with large open surfaces or even have a spring-like shape or spiral-shape to allow extra deformation of the 3D medical implant in parts of or over the whole 3D medical implant. Another shape that can be made to allow deformation is a short hollow tube or cylinder having a part of its envelope surface attached to the mesh surface.

The material of the support structure can be homogeneous, or can have through-holes, or can be porous with preferably open pores, or can have slits, or any combination of the above, to allow for rapid cell proliferation and tissue ingrowth.

The material of the support structure is characterized by having a thickness in an interval including 0.1 to 3.0 mm but more preferably in an interval including 0.1 to 1.0 mm. The height of a support structure is in an interval including 2.0-10.0 mm; more preferably in an interval including from 2.0 to 5.0 mm, such as 2.0, 2.5, 3.0, 3.5, 4.0, 4.5, or 5.0 mm.

Scaffold Component

According to the present disclosure, a scaffold component can have a substantially homogeneous interior, a porous interior, a fibrous interior, or a combination thereof. The scaffold component can be freestanding or can have a support structure which circumvents in whole or in part the structure of the scaffold component. The scaffold component serves as the underlying media for cells to proliferate on, a prerequisite for successful regeneration of new tissue. Such scaffold components can be made from natural or synthetic degradable porous material, degradable fibers or degradable hydrogels. Hydrogels are usually very fragile and do not tolerate mechanical loads very well. A support structure is therefore needed to allow the hydrogel to maintain its designed shape after implantation. The support structure defines the outer boundary of the scaffold component and also the height of the scaffold component. The support structure can also act as the contact point between the mesh and the scaffold component. The support structure can further act as the contact point between different mesh components if more than one mesh component is used to form the 3D matrix.

Various degradable hydrogels can be used as material for scaffold components. Especially gels made from natural polymers have been found to promote tissue proliferation. Various types of gels can be used such as, but not limited to, those based upon collagen, gelatin, fibrin, hyaluronic acid, alginate, chitosan, chondroitin sulphate and agarose. Such gels can also be crosslinked to better maintain integrity. Also synthetic hydrogels like those based upon polyethylene glycol in combination with lactide and glycolide and those further modified with acrylates to be photo crosslinked can be used. The hydrogels described above is only a short list of possible hydrogels that can be used as materials for scaffold components and can also be used in combination with other additives such as RGD, arginine-glycine-aspartic acid, peptide sequence to promote adhesion between cell and substrate, heparin and especially deactivated heparin to attract endogenous growth factors or even addition of growth factors to promote neovascularization as well as cell proliferation and differentiation of fibroblast and other cells. A hydrogel scaffold component can further be stabilized by fibers in a random or knitted structure. In an embodiment, the hydrogel is molded around the fiber structure. This embodiment is especially interesting when the hydrogel is freeze dried for shipping and storage.

A support structure is also required to allow certain open-structured, fibrous constructs to maintain their designed shape after implantation. When fibers are the preferred primary structure in a scaffold component according to the present disclosure, they are preferably made by melt spinning, wet spinning or electrospinning and the fibers can be deposited in a random fashion within the support structure or be oriented in a specific direction depending on the defect to be treated. The fibers are characterized by having either a glass transition temperature, Tg, higher than 40° C. or a melting point, Tm, of 50° C. or higher and by being made from degradable polymers, copolymers or blends of such polymers or copolymers being made from any of the monomers glycolide, lactide, paradioxanone, trimethylene carbonate, ethylene carbonate, ε-caprolactone, 1,5-dioxepan-2-one. Furthermore the degradable fibers can be made from polymers or blends mainly based upon poly-γ-butyrolactone or poly-β-butyrolactone or fibers derived from naturally derived materials such as chitosan and fibroin. Synthetic and naturally derived fibers can be mixed to achieve the intended function.

The scaffold component can also be made porous by using freeze drying, phase inversion techniques or simply by leaching or extraction of particulates such as salt or sugar particles. Porous scaffold components have been used in various constructs aimed for tissue engineering of various tissues but are difficult to design into a final device that will maintain its open porous function once implanted. If too stiff, the device may upset the immune system due to modulus mismatch and if too compliant it will usually collapse into a nonporous lump of material with no functionality. Inside a support structure like those described above, the porous material (as well as other types of scaffold material as described herein) will keep its shape being protected by the support structure from the load situation found at the implant site. This allows a design of porous hydrogels from natural polymers and also from structurally weak porous scaffold components characterized by having porosity higher than 50% and being made from degradable polymers with Tg less than 37° C. Examples of degradable polymers that will form soft and pliable porous scaffold components and are characterized by limited load-bearing capability are block-co-polymers that have a soft block (middle block) which account for at least 30% by weight of the scaffold component or more preferably more than 50% by weight. The material used in such scaffold components has a Tg which is less than 37° C. but more preferably less than 10° C. and even more preferably less than −10° C. Soft blocks fulfilling this criteria can be achieved by polytrimethylene carbonate, polyethylene carbonate or poly-1,5-dioxepanone-2-one alone or as copolymers between any of the monomers trimethylene carbonate, ethylene carbonate or 1,5-dioxepan-2-one in combination with any of the monomers ε-caprolactone, lactide, glycolide and paradioxanone. Any of the soft blocks can in a second polymerization step be further polymerized into a block-co-polymer by addition of any of the monomers lactide, glycolide, paradioxanone or ε-caprolactone. The so obtained block-co-polymer is characterized by having a melting point higher than 50° C. and having a crystallinity of at least 5%.

The freestanding scaffold component is made from degradable polymers or copolymers and may have a porous structure or be built up by fibers or any combination thereof. Porous materials for scaffold components are preferably made from, polymers or copolymers characterized by having a Tg higher than 40° C. or Tm higher than 50° C. These materials can be degradable polymers or copolymers, random or block, and also blends of degradable polymers or copolymers where the materials include one or more of the following monomers glycolide, lactide, paradioxanone, trimethylene carbonate, ε-caprolactone or 1,5-dioxepan-2-one. The material used in the porous scaffold component can also be made from polymers or copolymers of β-hydroxybutyrate or γ-hydroxybutyrate or copolymers containing ethylene carbonate units. When the freestanding scaffold component is made from fibers, the fibers need to have a certain diameter to ascertain the strength needed. Chopped fibers having diameter in an interval including 0.05 to 1.0 mm, and more preferably in an interval including 0.1 to 0.8 mm, can be glued together to form an open porous scaffold component of varied porosity that can also be combined with any of the hydrogels mentioned above or even smaller-sized fibers as those formed by electro spinning with a diameter in a range including 100 nm to 2000 nm, more preferably in the range including 300 nm to 1000 nm. The smaller-sized fibers can also be made by more conventional technique like melt-spinning or wet-spinning and can have a diameter in a range including 0.001 to 0.025 mm to further increase the area for cells to proliferate on.

The scaffold components with or without support structure may have different shapes in different areas and/or on different layers of the mesh to achieve different goals. Especially for such 3D medical implants that will be used in interfaces between hard and soft tissues, different mechanical properties are required in different parts of the implant, since bone cells will not readily grow on volume-building components that allow too much mobility while connective tissue is stimulated to grow on volume-building components that allow mobility.

The height of a scaffold component is in an interval including 2.0-10.0 mm; more preferably in an interval including from 2.0 to 5.0 mm, such as 2.0, 2.5, 3.0, 3.5, 4.5, or 5.0 mm.

The projected surface area of each volume-building component is in an interval including from 0.25 to 3.0 cm$^2$, such as 0.5, 0.75, 1.0, 1.5, 2.0, 2.5, or 3.0 cm$^2$.

15. The medical implant according to any one of the preceding claims, wherein the volume of each volume-building component is in an interval including from 0.12 to 3.0 cm$^3$, such as 0.12, 0.28, 0.5, 1.0, 1.5, 2.0, 2.5, or 3.0 cm$^3$.

Mesh Component

The function of the degradable mesh is to connect the volume-building components to each other and to keep them in place. In some applications, the mesh may advantageously also be load-bearing, i.e. able to withstand some of the tensile load exerted by the surrounding tissue when in an implanted state. The mesh that keeps the volume-building components in place is preferably made by jersey or warp knitting or can even be made by weaving or electrospinning. Both jersey and warp knitting can produce meshes with high porosity while weaving, electrospinning and meltblown process can make meshes with nearly no or very low porosity depending on the type of materials used to make the fibrous mesh and how dense these fibers appear in the structure. Low porosity mesh is preferably used in applications where there should be an impermeable or nearly impermeable barrier for a certain period of time so that different tissues with different needs can regenerate on either side of the mesh before the mesh is degraded and physical contact between the two different tissues occur. Preferably the porosity of such barriers should be less than 10% and more preferably less than 5% and have pore dimensions less than 50 µm and more preferably less than 25 µm to retard fibroblast through-growth and even more preferably less than 10 µm to nearly hinder fibroblast through-growth but still allow for neovascularization across the barrier.

The thickness of such low porosity meshes should preferably be less than 1.0 mm and more preferably less than 0.5 mm or even 0.25 mm. Especially when electrospinning or weaving are used to produce the mesh, the thickness is preferably 0.25 mm or even more preferably less than 0.15 mm.

Electrospinning is preferably used when the mesh should possess low porosity. Fibers obtained from electrospinning have a very small diameter typically in the range 100 nm up to 5 µm.

Meshes with low porosity made by electrospinning should preferably be made from fibers having diameters in the range including 0.1 to 2.0 µm and even more preferably in the range including 0.4 to 1.0 µm. Such thin fibers will be deposited in a random fashion at the collector and the number of fibers (layers) placed on top of each other will determine the thickness and porosity of the mesh.

A similar technique known as meltblown process can be used to make nonwoven mesh having various porosity and fiber diameter in the range 0.5 to 15 µm. Degradable polymers which can be meltblown are polymers and copolymers made from glycolide, lactide, paradioxanone, ε-caprolactone, trimethylene carbonate and 1,5-dioxepan-2-one. Other copolymers may be those having a soft block of ethylene carbonate units but also polymers or copolymers made from β-hydroxybutyrate or γ-hydroxybutyrate. Like electrospinning the porosity will depend on the number of layers deposited and the advantage compared to electrospinning is that it is much faster and the polymer does not need to be dissolved which is difficult with degradable polymers like glycolide and paradioxanone.

High porosity meshes with porosity larger than 10% is most easily made by jersey or warp knitting. Jersey knitting is the least preferable since this type of mesh will unravel if the doctor attempts to trim the medical implant with scalpel or a pair of scissors. The unraveling characteristics may be stopped by the volume-building components or the support structure but it is still a factor which may contribute to a less perfect medical implant. With warp knitting the unraveling is more difficult or not possible due to the interlocking character of the stiches formed. A variety of different knitting patterns can be achieved on warp knitting machines having from 2 or more bars. Each bar can be fed different types of fibers to achieve different mechanical properties in the mesh. Usually at least 2 guide bars are fed the same fiber to achieve a homogeneous mesh of the net type. Several patterns can be combined to achieve the property of interest and example of base structures that may be of interest for knitting various types of nets are pillar stitch open or closed, and various forms of displaced or interlaced pillar stitch to form knotless nets, various forms of tricot or atlas stitches can be used and inlay and marquisette stitches can further be used to strengthen the structures. Marquisette and pillar stitches can be used to produce square type net structure while displaced pillar stitches can be used to make rhombic or hexagonal type net structures. The stitches and nets mentioned are all highly deformable in all directions and the size of the opening together with the elasticity of the fibers used to knit the mesh determines the maximum deformation available.

The mesh component is substantially made of degradable homopolymers or copolymers, random or block, or blends of degradable synthetic polymers or copolymers which include one or more of the following monomers glycolide, lactide, paradioxanone, trimethylene carbonate, ε-caprolactone or 1,5-dioxepan-2-one, or polymers or copolymers of β-hydroxybutyrate or γ-hydroxybutyrate or copolymers containing ethylene carbonate units, or any combination thereof. Especially when the mesh is electrospun, a combination of the above mentioned materials with any of the degradable natural polymers collagen, gelatin, fibrin, hyaluronic acid, alginate, chitosan, chondroitin sulphate or naturally derived polymers fibroin and chitosan is especially interesting, but these natural or naturally derived materials can also be used in combination with melt spun, wet spun or meltblown fibers and also used as a coating.

The mesh suitably has a bending modulus of less than 4.0 MPa, preferably less than 2.5 MPa, and even more preferably less than 1.0 MPa. The test methodology as described in ASTM D1388 "Standard Test Method for Stiffness of Fabrics" can be used to define the flexural rigidity of the medical implant. Using the flexural rigidity, the bending modulus shall be calculated as described in Kenkare et al.; "Evaluation of drape characteristics in fabrics"; International Journal of Clothing Science and Technology 17(2), 109-123, 2005. For a medical implant having only one mesh component, the radius of curvature is governed by the bending modulus of the mesh component. If the mesh is highly flexible, the radius of curvature is near zero. The porosity of the mesh can be used to modulate the bendability of a medical implant holding two or more mesh components. With higher porosity mesh on the top of the medical implant, the medical implant will bend more, i.e. can attain a lower radius of curvature than if low porosity mesh is used. In combination with more elastic fibers the radius of curvature can be even less. For a medical implant with two mesh components, the radius of curvature in one direction should be at least 5 cm, such as 10, 15, or 20 cm. For a medical implant with more than two mesh components, the radius of curvature in one direction should be at least 10 cm, such as 15, 20, 25, or 30 cm. As an illustration, to support a small breast prosthesis, the medical implant according to the present disclosure should have a radius of curvature of approx. 5 cm or more. For implantation together with larger breast prostheses, the medical implant can be less flexible, and have a radius of curvature of approx. 5-15 cm. For abdominal wall applications, the medical implant can be even less flexible, and have a radius of curvature of approx. 10-20 cm.

Furthermore the number of needles per inch and the number of courses per inch as well as treading of the guidebars in the knitting machine will determine the porosity, i.e. size of the opening, of such meshes and can be varied over a great range. Various types of pillar stitch such as open or closed can be used to further strengthen the mesh in the vale direction while inlay or marquisette pattern can be used to strengthen the mesh in the course direction. The patterns mentioned above are just examples of very basic knitting patterns that can be used to achieve the properties of interest and shall not be limiting when it comes to combination of various knitting pattern well known to those skilled in the art of knitting. The warp knitted mesh should have a thickness in the range including 0.1 to 1.5 mm and more preferably in the range including 0.1 to 0.8 mm. The porosity of the knitted mesh should be found in the range including 10 to 80%, more preferably in the range including 20 to 60%.

The freedom to design is nearly unlimited due to the possibility to achieve various porosity and bending modulus and also different elongations at low load situations over the mesh with the use of the same material composition, but by varying the fiber thickness, the number of individual fibers being part of the multifilament as well as the use of different knitting patterns. Especially the use of warp knitting lends itself to nearly endless possibilities in terms of variation of knitting pattern with various degrees of porosity and mechanical properties. Such 2D knitted structures can be folded and combined in several ways to provide different 3D shapes kept apart by volume-building components which most conveniently can be made by 3D printing. The 3D printed structure itself may be much more than just volume-building and can easily be used to create a gradient compression modulus by choice of material or design of the 3D structure itself.

Within soft tissue regeneration there is a variety of different tissues having different requirements in terms of implant scaffold properties. Cell types, Young's modulus of the substrate and mechanical load situation over the defect area to be repaired or regenerated are just a few examples of the different macro factors that will contribute to a successful clinical outcome. The difference in load situation over a medical implant to be used for tendon or ligament regeneration compared to skin regeneration is just an example of the variety of properties needed and medical implants will presumably have to be tailored to each specific tissue type.

Preferred Clinical Applications for the 3D Medical Implant According to the Present Disclosure Breast Reconstruction After Mastectomy Not many years ago, breast cancer was equal to full removal of one or both breasts. Today, nipple sparing mastectomy gain more and more widespread ground, meaning that only the tissue directly affected by the cancer is removed and the full skin flap is preserved. Most patients in Europe and US today receive an implant in direct conjunction with the mastectomy. In US, an expander is often used for a short while before the implant is placed to heal the flap tissue before loaded with the implant. In Europe, the surgeon most often places the implant directly and uses a degradable collagen matrix or degradable mesh to keep the implant in place until new connective tissue have stabilized the implant.

The primary reason for using a mesh in this clinical indication is to stabilize the implant during the first 3 to 6 months before new connective tissue have been formed. Many times the flaps left behind after removal of the compromised tissue are very thin and with bad blood supply. It is therefore important to augment new vascularized connective tissue around the breast implant. Another indication for a medical implant according to the present disclosure is in the area of partial mastectomy where only a defined part of the breast/breast glands are removed. This often leads to soft tissue defects where the skin surface "sinks in" and need more connective tissue to fill the defect. Successful results have been achieved with 2D knitted mesh folded in several layers. The herein disclosed medical implant would secure space and thus allow tissue augmentation and use less foreign material and higher porosity to facilitate ingrowth and vascularization.

With a 2D mesh, only a certain thickness of new tissue can be augmented and there is a demand for 3D medical implants that would allow for a larger volume of new tissue to be formed. There are no current products on the market that can provide space for regeneration of extra connective tissue and at the same time be pliable to easy fit the contour of the breast implant. Furthermore, several plastic surgeons use fat grafting to fill the space around the breast implant. This is a relatively old but proven technique that gives good long term results if the fat cells do not migrate from the implant site. Using a 3D medical implant as disclosed herein with two or more knitted mesh components kept apart by 3D printed volume-building components filled with microfibers one could envision a medical implant that would be able to arrest or retain fat cells for a longer period of time and thus a better predictability of the clinical outcome.

Soft Tissue Augmentation 3D medical implants built from 2D knitted layers that are spaced equally or differently in different parts of the medical implant could be used as filler for augmentation or regeneration of compromised soft tissue after burns wounds or after removal of glands or cancer but also in selected cases of complex abdominal wall reconstruction after repeating recurrence. Such medical implants could be filled with collagen gels or microfibers and the geometry of the medical implant will be kept through 3D printed volume-building components, where such volume-building components can be made from degradable polymers having a high or low modulus depending on the load situation. The main function is to provide space and to have the space filled with a scaffold component where cells can attach and proliferate. For such medical implants used as fillers the mesh should preferably have a low area weight and thus made by thin fibers or multifilament having low linear density, i.e. denier number. Especially in aesthetic surgery where smaller areas need corrections these types of medical implants can be used to regenerate connective tissue and provide a better and more long lasting effect than various types of known fillers such as those based upon collagen or hyaluronic acid.

For abdominal wall at least one mesh needs to be very strong, bust strength >350 N, to act as a reinforcement and help to stabilize the wound to prevent dehiscence and/or late recurrence. These types of wounds will be helped by regeneration of new connective tissue why the medical implant disclosed herein having at least two mesh components joined together with volume building elements will provide space for such new connective tissue to regenerate. These medical implants can be placed onlay or inlay. The same type of medical implant can also be used to strengthen the tissue and to regenerate new connective tissue in patients undergoing colostomy. This is a clinical indication with high rate of hernia formation due to the weakening of the tissue made by the operative procedure itself.

Tendon/Ligament and Muscle Junction

Knitted scaffolds are ideal for muscle junction and tendon/ligament interface to bone. Knitted or woven fabric is not new as scaffold material during regeneration of tendons and ligaments. These structures are exposed to high stress and it is crucial for the outcome that space is preserved inside the scaffold for cells that will deposit new tissue to gradually take over the load during the regeneration. If the space is not preserved during the high stress cycles, cells may become damaged and thus necrotic which will compromise further regeneration. Only gradually the cells and the new tissue shall be exposed to the load situation. Thus, the medical implant according to the present disclosure, could for this application be envisioned as a rolled warp knitted tube with strong 3D printed volume-building components, which guarantees space for repopulation of cells during the first months of healing.

The invention claimed is:

1. A three-dimensional, degradable medical implant for regeneration of soft tissue comprising:
   a first plurality of volume-building components;
   a first warp-knitted mesh component which is substantially made of monofilament or multifilament fibers;
   wherein each volume-building component is attached to at least one point on a surface of the first mesh component, and the projected surface area of each volume-building component, when projected on the surface of the first mesh component, corresponds to a maximum of one tenth of the surface area of the first mesh component,
   wherein the first mesh component has a bending modulus of less than 4.0 MPa, and
   wherein the volume-building components are spaced apart by a distance of 0.2 mm to 5.0 mm.

2. The medical implant according to claim 1, wherein each of the volume-building components comprises a scaffold component, which scaffold component comprises a material which is chosen from (i) a hydrogel, (ii) a porous material, or (iii) fibers, or any combination thereof.

3. The medical implant according to claim 2, wherein at least one of the volume-building components further comprises a support structure, which is characterized by having a higher compression modulus than the scaffold component.

4. The medical implant according to claim 3, wherein the support structure of each of the volume-building components comprises (i) a frame-shaped structure, (ii) a spring-shaped structure, or (iii) a dome-shaped structure.

5. The medical implant according to claim 4, wherein the support structures of the plurality of volume-building components comprise the same shape chosen from (i)-(iii) or a combination of different shapes chosen from (i)-(iii).

6. The medical implant according to claim 3, wherein the support structure of at least one of the volume-building components has slits, pores or through-holes in its walls.

7. The medical implant according to claim 3, wherein the support structure is substantially made from degradable polymers synthesized from lactide, glycolide, paradioxanone, ε-caprolactone, trimethylene carbonate or any combination thereof in random or block copolymers, or amorphous variants, poly-D,L-lactide and amorphous copolymers between D,D- and L,L-lactide, or any combination thereof.

8. The medical implant according to claim 2, wherein the scaffold component comprises a hydrogel, and wherein the hydrogel of the scaffold component is substantially based upon collagen, gelatin, fibrin, hyaluronic acid, alginate, chitosan, chondroitin sulphate, agarose, polyethylene glycol as a block in copolymers with any of the monomers lactide, glycolide, trimethylene carbonate, ε-caprolactone or paradioxanone, or any combination thereof.

9. The medical implant according to claim 2, wherein the scaffold component comprises a porous material, wherein the porous material of the scaffold component is characterized by being degradable and having a Tg higher than 40° C. or a melting point higher than 50° C., and wherein the porous material comprises homopolymers or copolymers, random or block, or blends of such homopolymers or copolymers which include one or more of the following monomers glycolide, lactide, paradioxanone, trimethylene carbonate, ε-caprolactone or 1,5-dioxepan-2-one, or polymers or copolymers of β-hydroxybutyrate or γ-hydroxybutyrate or copolymers containing ethylene carbonate units, or any combination thereof.

10. The medical implant according to claim 2, wherein the scaffold component comprises fibers, and wherein the fibers of the scaffold component are substantially made of degradable homopolymers or copolymers, random or block, or blends of such homopolymers or copolymers synthesized from any of the monomers glycolide, lactide, paradioxanone, trimethylene carbonate, ethylene carbonate, ε-caprolactone, 1,5-dioxepan-2-one, polymers or blends mainly based upon poly-γ-butyrolactone or poly-β-butyrolactone, or fibers derived from natural occurring materials, chitosan, fibroin, or any combination thereof.

11. The medical implant according to claim 1, wherein the plurality of volume-building components comprises at least 5 volume-building components.

12. The medical implant according to claim 1, further comprising a second mesh component, which is attached to at least two of the first plurality of volume-building components, to create a sandwich structure.

13. The medical implant according to claim 1, wherein the projected surface area of each volume-building component is in an interval of 0.25 to 3.0 cm$^2$.

14. The medical implant according to claim 1, wherein the volume of each volume-building component is in an interval of 0.12 to 3.0 cm$^3$.

15. The medical implant according to claim 1, wherein at least one first mesh component is substantially made from degradable homopolymers, or copolymers, random or block, or blends of degradable homopolymers or copolymers which include one or more of the following monomers glycolide, lactide, paradioxanone, trimethylene carbonate, ε-caprolactone or 1,5-dioxepan-2-one, or polymers or copolymers of β-hydroxybutyrate or γ-hydroxybutyrate or copolymers containing ethylene carbonate units, or any combination thereof.

16. A medical implant according to claim 1 configured to stabilize a breast prosthesis and to provide space between flap tissue and the breast prosthesis to allow for tissue regeneration, wherein the medical implant is configured to be placed in close apposition to the breast prosthesis.

17. A three-dimensional, degradable medical implant for regeneration of soft tissue comprising:
 a first plurality of volume-building components; and
 a first warp-knitted mesh component which is substantially made of monofilament or multifilament fibers;
 wherein each volume-building component is attached to at least one point on a surface of the first mesh component, and the projected surface area of each volume-building component, when projected on the surface of the first mesh component, corresponds to a maximum of one tenth of the surface area of the first mesh component,
 wherein a second mesh component is attached to at least two of the first plurality of volume-building components, to create a sandwich structure, and
 wherein the first mesh component has a bending modulus of less than 4.0 MPa.

18. The medical implant according to claim 17, further comprising a second plurality of volume-building components, wherein each of the second plurality of volume-building components is attached to at least one surface of the second mesh component, to create a sandwich structure.

19. The medical implant according to claim 17, wherein the medical implant has a radius of curvature in one direction which is at least 5 cm.

20. The medical implant according to claim 17, further comprising a third mesh component, separated from the second mesh component by volume building components, wherein the medical implant has a radius of curvature in one direction which is at least 10 cm.

21. The medical implant according to claim 17 wherein the second mesh component is warp-knitted.

22. The medical implant according to claim 17, wherein the second mesh component has a bending modulus of less than 4.0 MPa.

23. A three-dimensional, degradable medical implant for regeneration of soft tissue comprising:
 a first plurality of volume-building components; and
 a first warp-knitted mesh component which is substantially made of monofilament or multifilament fibers;
 wherein each volume-building component is attached to at least one point on a surface of the first mesh component, and the projected surface area of each volume-building component, when projected on the surface of the first mesh component, corresponds to a maximum of one tenth of the surface area of the first mesh component,
 wherein the first mesh component has a bending modulus of less than 4.0 MPa, and
 wherein the projected surface area of each volume-building component is in an interval of 0.25 to 3.0 cm$^2$.

24. A three-dimensional, degradable medical implant for regeneration of soft tissue comprising:
 a first plurality of volume-building components; and
 a first warp-knitted mesh component which is substantially made of monofilament or multifilament fibers;
 wherein each volume-building component is attached to at least one point on a surface of the first mesh component, and the projected surface area of each volume-building component, when projected on the surface of the first mesh component, corresponds to a maximum of one tenth of the surface area of the first mesh component,
 wherein the first mesh component has a bending modulus of less than 4.0 MPa, and
 wherein the volume of each volume-building component is in an interval of 0.12 to 3.0 cm$^3$.

* * * * *